United States Patent
Al-Shafei et al.

(10) Patent No.: US 11,708,314 B2
(45) Date of Patent: *Jul. 25, 2023

(54) SYSTEMS AND PROCESSES FOR PRODUCING OLEFINS FROM CRUDE OIL

(71) Applicant: Saudi Arabian Oil Company, Dhahran (SA)

(72) Inventors: Emad Naji Al-Shafei, Dhahran (SA); Mohammed Z. Al-Bahar, Dhahran (SA); Ali Nader Al-Jishi, Dhahran (SA); Ki-Hyouk Choi, Dhahran (SA); Mohammad F. Al-Jishi, Dhahran (SA); Ali S. Al-Nasir, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/708,833

(22) Filed: Mar. 30, 2022

(65) Prior Publication Data

US 2022/0220047 A1    Jul. 14, 2022

Related U.S. Application Data

(63) Continuation of application No. 17/146,901, filed on Jan. 12, 2021, now Pat. No. 11,370,731.

(51) Int. Cl.
  *C07C 7/12*   (2006.01)
  *C07C 4/06*   (2006.01)
  (Continued)

(52) U.S. Cl.
  CPC .............. *C07C 7/005* (2013.01); *B01J 20/08* (2013.01); *B01J 20/28004* (2013.01);
  (Continued)

(58) Field of Classification Search
  None
  See application file for complete search history.

(56) References Cited

U.S. PATENT DOCUMENTS 3,944,481 A    3/1976   Wing et al.
6,632,351 B1   10/2003  Ngan et al.
(Continued)

FOREIGN PATENT DOCUMENTS

EP    0023802 A1    11/1981
JP    6166344 B2     7/2017
(Continued)

OTHER PUBLICATIONS

Franco et al., "Kinetic and thermodynamic equilibrium of asphaltenes sorption onto nanoparticles of nickel oxide supported on nanoparticulated alumina", Fuel 105, Elsevier, (2013), 408-414 (Year: 2013).*

(Continued)

*Primary Examiner* — Philip Y Louie
(74) *Attorney, Agent, or Firm* — Dinsmore & Shohl LLP

(57) ABSTRACT

A process for producing olefins from the hydrocarbon feed includes introducing the hydrocarbon feed into a Solvent Deasphalting Unit (SDA) to remove asphaltene from the hydrocarbon feed producing a deasphalted oil stream, wherein the SDA comprises a solvent that reacts with the hydrocarbon feed, and the deasphalted oil stream comprises from 0.01 weight percent (wt. %) to 18 wt. % asphaltenes; introducing the deasphalted oil stream into a steam catalytic cracking system; steam catalytically cracking the deasphalted oil stream in the steam catalytic cracking system in the presence of steam and a nano zeolite cracking catalyst to produce a steam catalytic cracking effluent; and separating the olefins from the steam catalytic cracking effluent.

16 Claims, 3 Drawing Sheets

(51) Int. Cl.
  *B01J 29/70* (2006.01)
  *C10G 21/00* (2006.01)
  *C07C 7/00* (2006.01)
  *B01J 20/08* (2006.01)
  *B01J 20/28* (2006.01)
  *B01J 21/04* (2006.01)
  *B01J 29/40* (2006.01)
  *B01J 35/00* (2006.01)

(52) U.S. Cl.
  CPC ............... *B01J 21/04* (2013.01); *B01J 29/40* (2013.01); *B01J 29/70* (2013.01); *B01J 35/006* (2013.01); *C07C 4/06* (2013.01); *C07C 7/12* (2013.01); *C10G 21/003* (2013.01); *C07C 2521/04* (2013.01); *C07C 2529/40* (2013.01); *C07C 2529/70* (2013.01); *C10G 2300/202* (2013.01); *C10G 2300/205* (2013.01); *C10G 2300/206* (2013.01); *C10G 2300/301* (2013.01); *C10G 2300/308* (2013.01)

(56) References Cited

U.S. PATENT DOCUMENTS

| | | | |
|---|---|---|---|
| 9,228,140 | B2 | 1/2016 | Abba et al. |
| 9,284,497 | B2 | 3/2016 | Bourane et al. |
| 9,382,486 | B2 | 7/2016 | Bourane et al. |
| 9,862,898 | B2 | 1/2018 | Ward et al. |
| 10,259,758 | B2 | 4/2019 | Ward et al. |
| 2013/0015100 | A1 | 1/2013 | Pereira Almao et al. |
| 2013/0228496 | A1 | 9/2013 | Bourane et al. |
| 2015/0152027 | A1 | 6/2015 | Shafi et al. |
| 2017/0029720 | A1 | 2/2017 | Koseoglu |
| 2017/0369397 | A1 | 12/2017 | Al-Herz et al. |
| 2018/0142168 | A1 | 5/2018 | Al-Ghamdi |
| 2018/0155633 | A1 | 6/2018 | Al-Ghamdi et al. |
| 2018/0187107 | A1 | 7/2018 | Abudawoud et al. |
| 2019/0055482 | A1* | 2/2019 | Salazar-Guillen ..... C10G 69/04 |
| 2019/0078023 | A1 | 3/2019 | Mahfouz et al. |

FOREIGN PATENT DOCUMENTS

| | | |
|---|---|---|
| KR | 20030078382 A | 10/2003 |
| WO | 2013188729 A1 | 12/2013 |
| WO | 2014094132 A1 | 6/2014 |
| WO | 2019018554 A2 | 1/2019 |

OTHER PUBLICATIONS

Alotaibi et al., "Enhancing the production of light olefins from heavy crude oils: Turning challenges into opportunities", Catalysis Today, vol. 317, pp. 86-98, Nov. 1, 2018.

International Search Report and Written Opinion pertaining to International Application No. PCT/US2021/019208 dated Sep. 22, 2021.

* cited by examiner

SYSTEMS AND PROCESSES FOR PRODUCING OLEFINS FROM CRUDE OIL

CROSS-REFERENCE TO RELATED APPLICATION

This application is a continuation application of U.S. patent application Ser. No. 17/146,901 filed Jan. 12, 2021, the entire disclosure of which is hereby incorporated herein by reference.

BACKGROUND

Field

The present disclosure relates to systems and processes for separating and upgrading petroleum-based hydrocarbons, in particular, systems and processes for separating and upgrading hydrocarbon feeds, such as crude oil, utilizing a deasphalting process in a solvent deasphalting unit prior to steam catalytic cracking.

Technical Background

The worldwide increase in demand for light olefins remains a major challenge for many integrated refineries. In particular, the production of some valuable light olefins such as ethylene, propene, and butene has attracted increased attention as purified olefin streams are considered the building blocks for polymer synthesis. The production of light olefins depends on several process variables, such as the feed type, operating conditions, and the type of catalyst. Despite the options available for producing a greater yield of propene and other light olefins, intense research activity in this field is still being conducted.

Petrochemical feeds, such as crude oils, can be converted to fuel blending components, chemical products, and intermediates, such as olefins and aromatic compounds, which are basic intermediates for a large portion of the petrochemical industry. Crude oil is conventionally processed by distillation followed by various reforming, solvent treatments, and hydroconversion processes to produce a desired slate of fuels, lubricating oil products, chemicals, chemical feedstocks, and the like. An example of a conventional refinery process includes distillation of crude oil by atmospheric distillation to recover gas oil, naphtha, gaseous products, and an atmospheric residue. Streams recovered from crude oil distillation at the boiling point of fuels have customarily been further processed to produce fuel components or greater value chemical products or intermediates.

Conventional refinery systems generally combine multiple complex refinery units with petrochemical plants. For example, conventional refinery systems employ atmospheric and vacuum distillation of crude oil followed by hydrocracking units to produce naphtha, liquefied petroleum gas (LPG), and other light fractions. Then, these materials are further processed in a steam cracker, a naphtha cracker, a reformer unit for benzene, toluene, and xylenes (BTX) production, a fluidized catalytic cracking unit, or a combination of these to produce olefins, such as olefins.

SUMMARY

Despite conventional refinery systems available for producing petrochemical products and intermediates from hydrocarbon feeds, these complex refinery systems often require many different unit operations for conversion of hydrocarbon feeds, such as crude oil, to greater value petrochemical products and intermediates, such as olefins.

Accordingly, there is an ongoing need for systems and processes to convert hydrocarbon feeds to olefins without the complexity of combining several refinery units. These needs are met by embodiments of systems and processes for producing olefins from the hydrocarbon feed described in the present disclosure. The systems and processes of the present disclosure comprise introducing the hydrocarbon feed into a solvent deasphalting unit (SDA) to remove asphaltene from the hydrocarbon feed and thereby producing a deasphalted oil stream. The SDA comprises a solvent that reacts with the hydrocarbon feed, and the deasphalted oil stream comprises from 0.01 weight percent (wt. %) to 18 wt. % asphaltenes. The deasphalted oil stream is introduced into a steam catalytic cracking system where the deasphalted oil stream is steam catalytically cracked in the steam catalytic cracking system in the presence of steam and a nano zeolite cracking catalyst to produce a steam catalytic cracking effluent. The olefins are separated from the steam catalytic cracking effluent. The systems and processes of the present disclosure utilize simple pre-treatment systems that require only one or few steps of pre-treatment prior to direct steam catalytic conversion of a deasphalted oil stream to olefins. Accordingly, the systems and processes of the present disclosure increase yield and production of greater value products and intermediates, such as olefins, with fewer unit operations and processing steps than conventional systems and processes, such as various combinations of hydrotreating units, reformers, aromatic recovery complexes, hydrocracking units, or fluidized catalytic cracking units. The systems and processes of the present disclosure may also increase yields of other valuable petrochemical products and intermediates, such as but not limited to gasoline blending components, benzene, toluene, xylenes, or combinations of these.

According to one or more other aspects of the present disclosure, a process for producing olefins from a hydrocarbon feed may include introducing the hydrocarbon feed into a Solvent Deasphalting Unit (SDA) to remove asphaltene from the hydrocarbon feed producing a deasphalted oil stream. The SDA may include a solvent that reacts with the hydrocarbon feed, and the deasphalted oil stream may include from 0.01 weight percent (wt. %) to 18 wt. % asphaltenes. The process may further include introducing the deasphalted oil stream into a steam catalytic cracking system, steam catalytically cracking the deasphalted oil stream in the steam catalytic cracking system in the presence of steam and a nano zeolite cracking catalyst to produce a steam catalytic cracking effluent, and separating the olefins from the steam catalytic cracking effluent.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
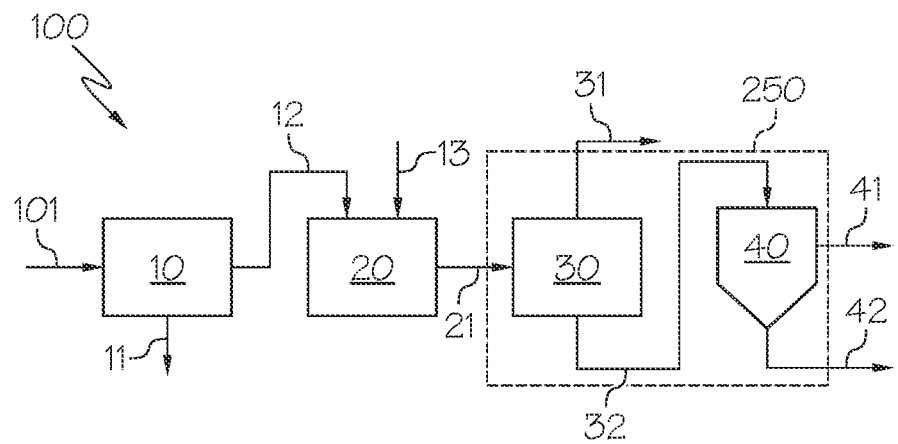
FIG. 1 schematically depicts a generalized flow diagram of a system for separating and upgrading crude oil, according to one or more embodiments shown and described in this disclosure.

For the purpose of describing the simplified schematic illustrations and descriptions of FIGS. 1-6, the numerous valves, temperature sensors, pressure sensors, electronic controllers and the like that may be employed and well known to those of ordinary skill in the art of certain chemical processing operations are not included. Further, accompanying components that are often included in chemical processing operations, such as, for example, air supplies, heat exchangers, surge tanks, or other related systems are not depicted. It would be known that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1-6. Mixing or combining may also include mixing by directly introducing both streams into the same reactor, separation device, or other system component. For example, it should be understood that when two streams are depicted as being combined directly prior to entering a separation unit or reactor, in some embodiments the streams could equivalently be introduced into the separation unit or reactor individually and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The present disclosure is directed to systems and processes for separating and upgrading hydrocarbon feeds, such as crude oil, to produce more valuable products and chemical intermediates, such as olefins. Referring to FIG. 1, one embodiment of a system 100 for upgrading a hydrocarbon feed 101 comprising crude oil or other heavy oil is schematically depicted. The system 100 may include a solvent deasphalting unit (SDA) 10, which may remove asphaltenes from the hydrocarbon feed 101 producing a deasphalted oil stream 12. The system 100 may further include a steam catalytic cracking system 20, which catalytically cracks the deasphalted oil stream 12 in the presence of steam 13 and a nano zeolite cracking catalyst to produce a steam catalytic cracking effluent 21. The system 100 may further include a steam catalytic cracking effluent separation system 250. The steam catalytic cracking effluent separation system 250 may include separation units that separate various components of the steam catalytic cracking effluent 21. According to embodiments, these separation units may include one or both of a gas and liquid separation unit 30, or a liquid and liquid separation unit 40. Either of these separation units may be disposed downstream of the steam catalytic cracking system 20.

The system 100 may be utilized in a process for separating and upgrading the hydrocarbon feed 101. The process for converting the hydrocarbon feed 101 may include introducing the hydrocarbon feed 101 into the SDA 10 to remove asphaltenes from the hydrocarbon feed 101 thereby producing a deasphalted oil stream 12. The SDA 10 comprises a solvent that reacts with the hydrocarbon feed 101 to aid in the removal of asphaltenes from the hydrocarbon feed 101. In embodiments, the deasphalted oil stream 12 comprises from 0.01 weight percent (wt. %) to 18 wt. % asphaltenes. The process may further include introducing the deasphalted oil stream 12 into the steam catalytic cracking system 20, and steam catalytically cracking the deasphalted oil stream 12 in the steam catalytic cracking system 20 in the presence of steam 13 and the nano zeolite cracking catalyst to produce the steam catalytic cracking effluent 21. The process may further include separating olefins from the steam catalytic cracking effluent 21.

The systems and processes of the present disclosure utilize a simple pre-treatment system that requires only one or few steps of pre-treatment prior to direct steam catalytic conversion of the hydrocarbon feed 101 to olefins. Accordingly, the systems and processes of the present disclosure increase yield and production of valuable products and intermediates, such as olefins including ethylene, propylene, butenes, or combinations of these, with less equipment and process units, such as distillation units, hydrotreating units, hydrocracking units, fluidized catalytic cracking units, or combinations of these. The steam catalytic cracking system 20 may use 25 to 50 times less catalyst and may be operated with a longer time on stream compared to fluidized catalytic cracking units for producing olefins, among other benefits.

As used in this disclosure, a "reactor" refers to any vessel, container, or the like, in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. As used in the present disclosure, the term "fixed bed reactor" may refer to a reactor in which a catalyst is confined within the reactor in a reaction zone in the reactor and is not circulated continuously through a reactor and regenerator system.

As used in this disclosure, one or more "reaction zones" may be disposed within a reactor. As used in this disclosure, a "reaction zone" refers to an area in which a particular reaction takes place in a reactor. For example, a packed bed reactor with multiple catalyst beds may have multiple reaction zones, in which each reaction zone is defined by the area of each catalyst bed.

As used in this disclosure, a "separation unit" refers to any separation device that at least partially separates one or more chemicals in a mixture from one another. For example, a separation unit may selectively separate different chemical species from one another, forming one or more chemical fractions. Examples of separation units include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided or separated into two or more process streams of desired composition.

As used in this disclosure, the term "fractionation" may refer to a process of separating one or more constituents of a composition in which the constituents are divided from each other during a phase change based on differences in properties of each of the constituents. As an example, as used in this disclosure, "distillation" refers to separation of constituents of a liquid composition based on differences in the boiling point temperatures of constituents of a composition, either at atmospheric conditions or under negative pressure. As used in this disclosure, the term "vacuum distillation" may refer to distillation conducted under a negative pressure relative to atmospheric pressure.

As used in this disclosure, the terms "upstream" and "downstream" may refer to the relative positioning of unit operations with respect to the direction of flow of the process streams. A first unit operation of the system may be considered "upstream" of a second unit operation if process streams flowing through the system encounter the first unit operation before encountering the second unit operation. Likewise, a second unit operation may be considered "downstream" of the first unit operation if the process streams flowing through the system encounter the first unit operation before encountering the second unit operation.

As used in the present disclosure, passing a stream or effluent from one unit "directly" to another unit may refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined. Surge vessels are also not considered to be intervening systems that change the composition of a stream or effluent.

As used in this disclosure, the term "initial boiling point" or "IBP" of a composition may refer to the temperature at which the constituents of the composition with the least boiling point temperatures begin to transition from the liquid phase to the vapor phase. As used in this disclosure, the term "end boiling point" or "EBP" of a composition may refer to the temperature at which the greatest boiling temperature constituents of the composition transition from the liquid phase to the vapor phase. A hydrocarbon mixture may be characterized by a distillation profile expressed as boiling point temperatures at which a specific weight percentage of the composition has transitioned from the liquid phase to the vapor phase.

As used in this disclosure, the term "atmospheric boiling point temperature" may refer to the boiling point temperature of a compound at atmospheric pressure.

As used in this disclosure, the term "effluent" may refer to a stream that is passed out of a reactor, a reaction zone, or a separation unit following a particular reaction or separation. Generally, an effluent has a different composition than the stream that entered the separation unit, reactor, or reaction zone. It should be understood that when an effluent is passed to another system unit, only a portion of that system stream may be passed. For example, a slip stream may carry some of the effluent away, meaning that only a portion of the effluent may enter the downstream system unit. The term "reaction effluent" may more particularly be used to refer to a stream that is passed out of a reactor or reaction zone.

As used in this disclosure, a "catalyst" may refer to any substance that increases the rate of a specific chemical reaction. Catalysts described in this disclosure may be utilized to promote various reactions, such as, but not limited to, steam cracking, aromatic cracking, hydrodearylation, hydrotreating, reforming, isomerization, or combinations thereof. However, some catalysts described in the present disclosure may have multiple forms of catalytic activity, and calling a catalyst by one particular function does not render that catalyst incapable of being catalytically active for other functionality.

As used in this disclosure, "cracking" generally refers to a chemical reaction where a molecule having carbon-carbon bonds is broken into more than one molecule by the breaking of one or more of the carbon-carbon bonds; where a compound including a cyclic moiety, such as an aromatic compound, is converted to a compound that does not include a cyclic moiety; or where a molecule having carbon-carbon double bonds are reduced to carbon-carbon single bonds.

As used in this disclosure, the term "size" or "crystal size" may refer to an average particle diameter of alumina oxide, or nano-zeolite cracking catalyst when the alumina oxide or nano-zeolite cracking catalyst is in the form of spherical particles, or may refer to a length of a major axis of alumina oxide or nano-zeolite cracking catalyst when the alumina oxide or nano-zeolite cracking catalyst is not in a spherical form, for example, in the form of non-spherical particles.

As used in this disclosure, the term "crude oil" or "whole crude oil" is to be understood to mean a mixture of petroleum liquids, gases, or combinations of liquids and gases, including, in some embodiments, impurities such as but not limited to sulfur-containing compounds, nitrogen-containing compounds, and metal compounds, that have not undergone significant separation or reaction processes. Crude oils are distinguished from fractions of crude oil. In certain embodiments, the crude oil feedstock may be a minimally treated light crude oil to provide a crude oil feedstock having total metals (Ni+V) content of less than 5 parts per million by weight (ppmw) and Conradson carbon residue of less than 5 wt. %.

It should further be understood that streams may be named for the components of the stream, and the component for which the stream is named may be the major component of the stream (such as comprising from 50 wt. %, from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrogen stream" passing to a first system component or from a first system component to a second system component should be understood to equivalently disclose "hydrogen" passing to the first system component or passing from a first system component to a second system component.

Referring again to FIG. 1, an embodiment of the system 100 for separating and upgrading the hydrocarbon feed 101 is schematically depicted. As previously discussed, the system 100 may include the SDA 10 and the steam catalytic cracking system 20 downstream of the SDA 10. The system 100 may further include the steam catalytic cracking effluent separation system 250. The steam catalytic cracking effluent separation system 250 may include separation units that separate various components of the steam catalytic cracking effluent 21. According to embodiments, these separation units may include one or both of a gas and liquid separation unit 30, or a liquid and liquid separation unit 40. Either of these separation units may be disposed downstream of the steam catalytic cracking system 20.

The hydrocarbon feed 101 may include one or more heavy oils, such as but not limited to crude oil, vacuum residue, tar sands, bitumen, other heavy oil streams, or combinations of these. It should be understood that, as used in this disclosure, a "heavy oil" may refer to a raw hydrocarbon, such as whole crude oil, which has not been previously processed through distillation, or may refer to a hydrocarbon oil, which has undergone some degree of processing prior to being introduced into the system 100 as the hydrocarbon feed 101. The hydrocarbon feed 101 may have a density of greater than or equal to 0.80 grams per milliliter. The hydrocarbon feed 101 may have an end boiling point (EBP) of greater than 565° C. The hydrocarbon feed 101 may have a concentration of nitrogen of less than or equal to 3000 parts per million by weight (ppmw).

In embodiments, the hydrocarbon feed 101 may be a crude oil, such as a whole crude oil. The crude oil may have an American Petroleum Institute (API) gravity of from 25 degrees to 50 degrees. For example, the hydrocarbon feed 101 may include a light crude oil, a heavy crude oil, or combinations of these. Example properties for an exemplary grade of Arab light crude oil are listed in Table 1.

TABLE 1

Example of Arab Light Export Feedstock

| Analysis | Units | Value | Test Method |
|---|---|---|---|
| American Petroleum Institute (API) gravity | degree | 33.13 | ASTM D287 |
| Density | grams per milliliter (g/mL) | 0.8595 | ASTM D287 |
| Carbon Content | weight percent (wt. %) | 85.29 | ASTM D5291 |
| Hydrogen Content | wt. % | 12.68 | ASTM D5292 |
| Sulfur Content | wt. % | 1.94 | ASTM D5453 |
| Nitrogen Content | parts per million by weight (ppmw) | 849 | ASTM D4629 |
| Asphaltenes | wt. % | 1.2 | ASTM D6560 |
| Micro Carbon Residue (MCR) | wt. % | 3.4 | ASTM D4530 |
| Vanadium (V) Content | ppmw | 15 | IP 501 |
| Nickel (Ni) Content | ppmw | 12 | IP 501 |
| Arsenic (As) Content | ppmw | 0.04 | IP 501 |
| Boiling Point Distribution | | | |
| Initial Boiling Point (IBP) | Degrees Celsius (° C.) | 33 | ASTM D7169 |
| 5% Boiling Point (BP) | ° C. | 92 | ASTM D7169 |
| 10% BP | ° C. | 133 | ASTM D7169 |
| 20% BP | ° C. | 192 | ASTM D7169 |
| 30% BP | ° C. | 251 | ASTM D7169 |
| 40% BP | ° C. | 310 | ASTM D7169 |
| 50% BP | ° C. | 369 | ASTM D7169 |
| 60% BP | ° C. | 432 | ASTM D7169 |
| 70% BP | ° C. | 503 | ASTM D7169 |
| 80% BP | ° C. | 592 | ASTM D7169 |
| 90% BP | ° C. | >720 | ASTM D7169 |
| 95% BP | ° C. | >720 | ASTM D7169 |
| End Boiling Point (EBP) | ° C. | >720 | ASTM D7169 |
| BP range C5-180° C. | wt. % | 18.0 | ASTM D7169 |
| BP range 180° C.-350° C. | wt. % | 28.8 | ASTM D7169 |
| BP range 350° C.-540° C. | wt. % | 27.4 | ASTM D7169 |
| BP range >540° C. | wt. % | 25.8 | ASTM D7169 |

Weight percentages in Table 1 are based on the total weight of the crude oil.

When the hydrocarbon feed 101 comprises a crude oil, the crude oil may be a whole crude or may be a crude oil that has undergone at some processing, such as desalting, solids separation, or scrubbing. For example, the hydrocarbon feed 101 may be a de-salted crude oil that has been subjected to a de-salting process. In embodiments, the hydrocarbon feed 101 may include a crude oil that has not undergone pretreatment, separation (such as distillation), or other operation that changes the hydrocarbon composition of the crude oil prior to introducing the crude oil to the system 100.

A process for converting a hydrocarbon feed 101 to olefins according to one or more embodiments will now be described with reference again to FIG. 1. The hydrocarbon feed 101 may be fluidly coupled to the SDA 10, so that the hydrocarbon feed 101 may be introduced into the SDA 10. The SDA 10 may operate to remove asphaltene compounds from the hydrocarbon feed 101 to produce a deasphalted residue stream 11, and a deasphalted oil stream 12 that may be passed to the steam catalytic cracking system 20. Passing the deasphalted oil stream 12 to the steam catalytic cracking system 20 may further increase the conversion of the hydrocarbon feed 101 to olefins in the system 100. The SDA 10 may be disposed upstream of the steam catalytic cracking system 20.

The deasphalted oil stream 12 may have from 0.01 weight percent (wt. %) to 18 wt. % asphaltenes. In embodiments, the deasphalted oil stream 12 may have from 0.1 wt. % to 18 wt. %, from 1 wt. % to 18 wt. %, from 2 wt. % to 18 wt. %, from 5 wt. % to 18 wt. %, from 0.01 wt. % to 15 wt. %, from 1 wt. % to 15 wt. %, from 2 wt. % to 15 wt. %, or from 5 wt. % to 15 wt. % asphaltenes.

The SDA 10 contains a solvent. The solvent may comprise propane, butane, pentane, or combinations of these. In embodiments, a solvent-to-oil (hydrocarbon feed 101) volume ratio is from 2:1 to 50:1, 3:1 to 50:1, 4:1 to 50:1, 5:1 to 50:1, 2:1 to 45:1, or 2:1 to 40:1. The solvent may, according to embodiments, be selected based upon the feed. For example, propane may be used as the solvent for crude oil, and a mixture of propane and butane may be used as the solvent for oil stripped from LPG.

The system 100 includes the steam catalytic cracking system 20. The steam catalytic cracking system 20 may be disposed downstream of the SDA 10. The steam catalytic cracking system 20 may operate to contact the deasphalted oil stream 12 with steam 13 in the presence of a nano-zeolite cracking catalyst to produce a steam catalytic cracking effluent 21.

Figure 2:
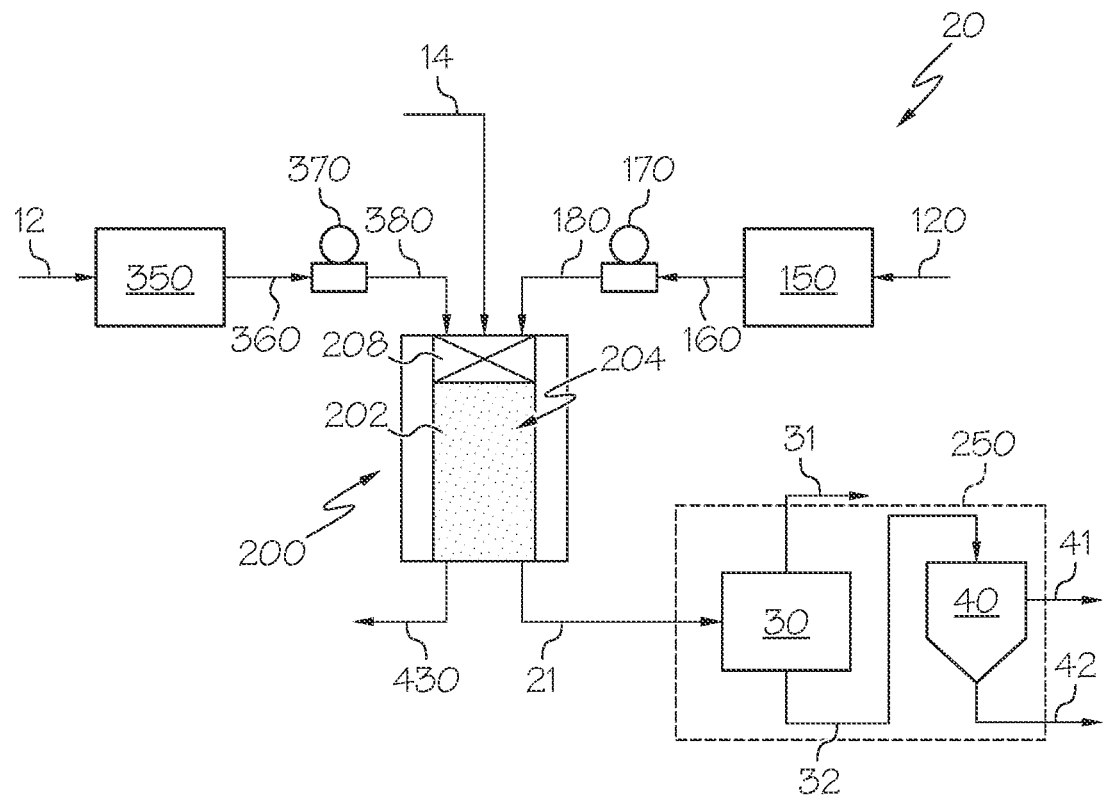
FIG. 2 schematically depicts a generalized flow diagram of a steam catalytic cracking system and steam catalytic cracking effluent separation system of the system for separating and upgrading crude oil in FIG. 1, according to one or more embodiments shown and described in this disclosure.

Referring now to FIG. 2, a simplified schematic illustration of one particular embodiment of the steam catalytic cracking system 20 is graphically depicted. It should be understood that other configurations of the steam catalytic cracking system 20 may be suitable for incorporation into the system 100 for converting hydrocarbon feeds to olefins. The steam catalytic cracking system 20 may include one or a plurality of steam catalytic cracking reactors 200. The steam catalytic cracking reactor 200 may be a fixed bed catalytic cracking reactor that includes a cracking catalyst 202 disposed within a steam cracking catalyst zone 204. The steam catalytic cracking reactor 200 may include a porous packing material 208, such as silica carbide packing, upstream of the steam cracking catalyst zone 204. The porous packing material 208 may ensure sufficient heat transfer to the deasphalted oil stream 12 and steam prior to conducting the steam catalytic cracking reaction in the steam cracking catalyst zone 204.

The cracking catalyst may be a nano-zeolite cracking catalyst comprising nano-zeolite particles. A variety of nano-zeolites may be suitable for the steam catalytic cracking reactions in the steam catalytic cracking reactor 200. The nano-zeolite cracking catalyst may include a structured zeolite, such as an MFI or BEA structured zeolite, for example. In embodiments, the nano-zeolite cracking catalyst may comprise nano ZSM-5 zeolite, nano BEA zeolite, or both. In embodiments, the nano-zeolite cracking catalyst may include a combination of nano ZSM-5 zeolite and nano BEA zeolite. The nano-zeolites, such as nano-ZSM-5, nano Beta zeolite, or both may be in hydrogen form. In hydrogen form, the Brønsted acid sites in the zeolite, also known as bridging $O_H$—H groups, may form hydrogen bonds with other framework oxygen atoms in the zeolite framework.

The nano ZSM-5 zeolite, the nano Beta zeolite, or both may have a molar ratio of silica to alumina to provide sufficient acidity to the nano-zeolite cracking catalyst to conduct the steam catalytic cracking reactions. The nano-ZSM-5 zeolite, nano Beta zeolite, or both, may have a molar ratio of silica to alumina of from 10 to 200, from 15 to 200, from 20 to 200, from 10 to 150, from 15 to 150, or from 20 to 150. The nano-ZSM-5 zeolite, nano Beta zeolite, or both combined, may have total acidity in the range of 0.2 to 2.5 mmol/g, 0.3 to 2.5 mmol/g, 0.4 to 2.5 mmol/g, 0.5 to 2.5 mmol/g, 0.2 to 2.0 mmol/g, 0.3 to 2.0 mmol/g, 0.4 to 2.0 mmol/g, or 0.5 to 2.0 mmol/g. The nano-ZSM-5 zeolite, nano Beta zeolite, or both combined, may contain Brønsted acid sites in the range of 0.1 to 1.0 mmol/g, 0.2 to 1.0 mmol/g, 0.3 to 1.0 mmol/g, 0.1 to 0.9 mmol/g, 0.2 to 0.9 mmol/g, or 0.3 to 0.9 mmol/g. The concentration of Brønsted acid sites may be determined by Pyridine Fourier-transform infrared spectroscopy (FTIR) using a pyridine molecule as a probe molecule and introduced to the cell to saturate the sample and was evacuated at 150° C. The obtained peaks at approximately 1540 and 1450 cm$^{-1}$ represented Brønsted and Lewis acid sites respectively. The nano-ZSM-5 zeolite, nano Beta zeolite, or both, may have an average crystal size of from 50 nanometer (nm) to 600 nm, from 60 nm to 600 nm, from 70 nm to 600 nm, from 80 nm to 600 nm, from 50 nm to 580 nm, or from 50 nm to 550 nm. The average crystal size may be measured using the Scanning Electron Microscopy (SEM) technique.

The nano-zeolite cracking catalyst may also include an alumina binder, which may be used to consolidate the nanoparticles of nano ZSM-5 zeolite, nano Beta zeolite, or both to form the nano-zeolite cracking catalyst. The nano-zeolite cracking catalyst may be prepared by combining the nano ZSM-5 zeolite, the nano Beta zeolite, or both with the aluminum binder and extruding the nano-zeolite cracking catalyst to form pellets or other catalyst shapes. The nano-zeolite cracking catalyst may include from 10 weight percent (wt. %) to 80 wt. %, from 10 wt. % to 75 wt. %, from 10 wt. % to 70 wt. %, from 15 wt. % to 80 wt. %, from 15 wt. % to 75 wt. %, or from 15 wt. % to 70 wt. % alumina binder based on the total weight of the nano-zeolite cracking catalyst. The nano-zeolite cracking catalyst may have a mesoporous to microporous volume ratio in the range of from 0.5 to 1.5, from 0.6 to 1.5, from 0.7 to 1.5, from 0.5 to 1.0, from 0.6 to 1.0, or from 0.7 to 1.0.

Referring again to FIG. 2, the deasphalted oil stream 12 may be introduced to the steam catalytic cracking reactor 200. Prior to introducing the deasphalted oil stream 12 into the steam catalytic cracking reactor 200, the deasphalted oil stream 12 may be collected in a crude oil tank 350, according to one or more embodiments. The deasphalted oil stream 12 may be heated to a temperature of from 35 degrees Celsius (° C.) to 150° C. and then introduced to a feed pump 370 through line 360. In embodiments, the deasphalted oil stream 12 may be heated from 40° C. to 150° C., from 45° C. to 150° C., from 50° C. to 150° C., from 35° C. to 145° C., from 40° C. to 145° C., from 45° C. to 145° C., from 35° C. to 140° C., from 40° C. to 140° C., or from 45° C. to 140° C. The flowrate of the feed pump 370 may be adjusted so that the deasphalted oil stream 12 is injected into the steam catalytic cracking reactor 200 through line 380 at a gas hourly space velocity of greater than or equal to 0.1 per hour ($h^{-1}$) or greater than or equal to 0.25 $h^{-1}$. The deasphalted oil stream 12 may be injected into the steam catalytic cracking reactor 200 at a gas hourly space velocity of less than or equal to 50 $h^{-1}$, less than or equal to 25 $h^{-1}$, less than or equal to 20 $h^{-1}$, less than or equal to 14 $h^{-1}$, less than or equal to 9 $h^{-1}$, or less than or equal to 5 $h^{-1}$. The deasphalted oil stream 12 may be injected into the steam catalytic cracking reactor 200 at a gas hourly space velocity of from 0.1 per hour ($h^{-1}$) to 50 $h^{-1}$, from 0.1 $h^{-1}$ to 25 $h^{-1}$, from 0.1 $h^{-1}$ to 20 $h^{-1}$, from 0.1 $h^{-1}$ to 14 $h^{-1}$, from 0.1 $h^{-1}$ to 9 $h^{-1}$, from 0.1 $h^{-1}$ to 5 $h^{-1}$, from 0.1 $h^{-1}$ to 4 $h^{-1}$, from 0.25 $h^{-1}$ to 50 $h^{-1}$, from 0.25 $h^{-1}$ to 25 $h^{-1}$, from 0.25 $h^{-1}$ to 20 $h^{-1}$, from 0.25 $h^{-1}$ to 14 $h^{-1}$, from 0.25 $h^{-1}$ to 9 $h^{-1}$, from 0.25 $h^{-1}$ to 5 $h^{-1}$, from 0.25 $h^{-1}$ to 4 $h^{-1}$, from 1 $h^{-1}$ to 50 $h^{-1}$, from 1 $h^{-1}$ to 25 $h^{-1}$, from 1 $h^{-1}$ to 20 $h^{-1}$, from 1 $h^{-1}$ to 14 $h^{-1}$, from 1 $h^{-1}$ to 9 $h^{-1}$, or from 1 $h^{-1}$ to 5 $h^{-1}$ via the preheated line 380. The deasphalted oil stream 12 may be further pre-heated in the line 380 to a temperature between 100° C. to 250° C. before injecting the deasphalted oil stream 12 into the steam catalytic cracking reactor 200.

Water 120 may be injected to the steam catalytic cracking reactor 200 through lines 160, 180 via the water feed pump 170. Prior to introducing the water 120 into the steam catalytic cracking reactor 200, the water 120 may be collected in a water tank 150. The water line 180 may be pre-heated to a temperature of from 50° C. to 75° C., from 50° C. to 70° C., from 55° C. to 75° C., or from 55° C. to 70° C. The water 120 may be converted to steam in water line 180 or upon contacting with the deasphalted oil stream 12 in the steam catalytic cracking reactor 200. The flowrate of the water feed pump 170 may be adjusted to deliver water 120 (liquid, steam, or both) to the steam catalytic cracking reactor 200 at a gas hourly space velocity of greater than or equal to 0.1 $h^{-1}$, greater than or equal to 0.5 $h^{-1}$, greater than or equal to 1 $h^{-1}$, greater than or equal to 5 $h^{-1}$, greater than or equal to 6 $h^{-1}$, greater than or equal to 10 $h^{-1}$, or even greater than or equal to 15 $h^{-1}$. The water 120 may be introduced to the steam catalytic cracking reactor 200 at a gas hourly space velocity of less than or equal to 100 $h^{-1}$, less than or equal to 75 $h^{-1}$, less than or equal to 50 $h^{-1}$, less than or equal to 30 $h^{-1}$, or less than or equal to 20 $h^{-1}$. The water 120 may be introduced to the steam catalytic cracking reactor 200 at a gas hourly space velocity of from 0.1 $h^{-1}$ to 100 $h^{-1}$, from 0.1 $h^{-1}$ to 75 $h^{-1}$, from 0.1 $h^{-1}$ to 50 $h^{-1}$, from 0.1 $h^{-1}$ to 30 $h^{-1}$, from 0.1 $h^{-1}$ to 20 $h^{-1}$, from 1 $h^{-1}$ to 100 $h^{-1}$, from 1 $h^{-1}$ to 75 $h^{-1}$, from 1 $h^{-1}$ to 50 $h^{-1}$, from 1 $h^{-1}$ to 30 $h^{-1}$, from 1 $h^{-1}$ to 20 $h^{-1}$, from 5 $h^{-1}$ to 100 $h^{-1}$, from 5 $h^{-1}$ to 75 $h^{-1}$, from 5 $h^{-1}$ to 50 $h^{-1}$, from 5 $h^{-1}$ to 30 $h^{-1}$, from 5 $h^{-1}$ to 20 $h^{-1}$, from 6 $h^{-1}$ to 100 $h^{-1}$, from 6 $h^{-1}$ to 75 $h^{-1}$, from 6 $h^{-1}$ to 50 $h^{-1}$, from 6 $h^{-1}$ to 30 $h^{-1}$, from 6 $h^{-1}$ to 20 $h^{-1}$, from 10 $h^{-1}$ to 100 $h^{-1}$, from 10 $h^{-1}$ to 75 $h^{-1}$, from 10 $h^{-1}$ to 50 $h^{-1}$, from 10 $h^{-1}$ to 30 $h^{-1}$, from 10 $h^{-1}$ to 20 $h^{-1}$, from 15 $h^{-1}$ to 100 $h^{-1}$, from 15 $h^{-1}$ to 75 $h^{-1}$, from 15 $h^{-1}$ to 50 $h^{-1}$, from 15 $h^{-1}$ to 30 $h^{-1}$, or from 15 $h^{-1}$ to 20 $h^{-1}$ via water line 180.

The steam from injection of the water 120 may reduce the hydrocarbon partial pressure, which may have the dual effects of increasing yields of light olefins (e.g., ethylene, propylene and butylene) as well as reducing coke formation. Light olefins like propylene and butylene are mainly generated from catalytic cracking reactions following the carbonium ion mechanism, and as these are intermediate products, they can undergo secondary reactions such as hydrogen transfer and aromatization (leading to coke formation). The steam may increase the yield of light olefins by suppressing these secondary bi-molecular reactions, and reduce the concentration of reactants and products, which favor selectivity towards light olefins. The steam may also suppress secondary reactions that are responsible for coke formation on catalyst surface, which is good for catalysts to maintain high average activation. These factors may show that a large steam-to-oil weight ratio may be beneficial to the production of light olefins.

The gas hourly space velocity of water 120 introduced to the steam catalytic cracking reactor 200 may be greater than the gas hourly space velocity of the deasphalted oil stream 12 passed to the steam catalytic cracking reactor 200. A ratio of the flowrate (gas hourly space velocity) of steam or water 120 to the flowrate (gas hourly space velocity) of deasphalted oil stream 12 to the steam catalytic cracking reactor 200 may be from 2 to 10 times, from 2 to 8 times, 2 to 6, from 2 to 5.5, from 2 to 5, from 3 to 6, from 3 to 5.5, or from 3 to 5 to improve the steam catalytic cracking process in the presence of the nano-zeolite cracking catalyst.

Referring still to FIG. 2, the steam catalytic cracking reactor 200 may be operable to contact the deasphalted oil stream 12 with steam (from water 120) in the presence of the nano-zeolite cracking catalyst under reaction conditions sufficient to cause at least a portion of the hydrocarbons from the deasphalted oil stream 12 to undergo one or more cracking reactions to produce a steam catalytic cracking effluent 21 comprising one or a plurality of olefins. The olefins may include ethylene, propylene, butenes, or combinations of these. The steam catalytic cracking reactor 200 may be operated at a temperature of greater than or equal to 525° C., greater than or equal to 550° C., or even greater than or equal to 575° C. The steam catalytic cracking reactor 200 may be operated at a temperature of less than or equal to 750° C., less than or equal to 675° C., less than or equal to 650° C., or even less than or equal to 625° C. The steam catalytic cracking reactor 200 may be operated at a temperature of from 525° C. to 750° C., from 525° C. to 675° C., from 525° C. to 650° C., from 525° C. to 625° C., from 550° C. to 675° C., from 550° C. to 650° C., from 550° C. to 625° C., from 575° C. to 675° C., from 575° C. to 650° C., or from 575° C. to 625° C. The process may operate at atmospheric pressure (approximately from 1 to 2 bar).

The steam catalytic cracking reactor 200 may be operated in a semi-continuous manner. For example, during a conversion cycle, the steam catalytic cracking reactor 200 may be operated with the deasphalted oil stream 12 and water 120 flowing to the steam catalytic cracking reactor 200 for a period of time, at which point the catalyst may be regenerated. Each conversion cycle of the steam catalytic cracking reactor 200 may be from 1 to 8 hours, from 1 to 6 hours, from 1 to 4 hours, from 2 to 8 hours, from 2 to 6 hours, or from 2 to 4 hours before switching off the feed pump 370 and the water pump 170. At the end of the conversion cycle, the flow of deasphalted oil stream 12 and water 120 may be stopped and the nano-zeolite cracking catalyst may be regenerated during a regeneration cycle. In embodiments, the steam catalytic cracking system 20 may include a plurality of steam catalytic cracking reactors 200, which can be operated in parallel or in series. With a plurality of steam catalytic cracking reactors 200 operating in parallel, one or more of the steam catalytic cracking reactors 200 can continue in a conversion cycle while one or more of the other steam catalytic cracking reactors 200 are taken off-line for regeneration of the nano-zeolite cracking catalyst, thus maintaining continuous operation of the steam catalytic cracking system 20.

Referring to FIG. 2, during a regeneration cycle, the steam catalytic cracking reactor 200 may be operated to regenerate the nano-zeolite cracking catalyst. The nano-zeolite cracking catalyst may be regenerated to remove coke deposits accumulated during the conversion cycle. To regenerate the nano-zeolite cracking catalyst, hydrocarbon gas and liquid products produced by the steam catalytic cracking process may be evacuated from the steam catalytic cracking reactor 200. Nitrogen gas may be introduced to the steam catalytic cracking reactor 200 through gas line 14 to evacuate the hydrocarbon gas and liquid products from the fixed bed steam catalytic cracking reactor 200. Nitrogen may be introduced to the steam catalytic cracking reactor 200 at gas hourly space velocity of from 10 per hour ($h^{-1}$) to 100 $h^{-1}$.

Following evacuation of the hydrocarbon gases and liquids, air may be introduced to the steam catalytic cracking reactor 200 through gas line 14 at a gas hourly space velocity of from 10 $h^{-1}$ to 100 $h^{-1}$. The air may be passed out of the steam catalytic cracking reactor 200 through line 430. While passing air through the nano-zeolite cracking catalyst in the steam catalytic cracking reactor 200, the temperature of the steam catalytic cracking reactor 200 may be increased from the reaction temperature to a regeneration temperature of from 650° C. to 750° C. for a period of from 3 hours to 5 hours. The gas produced by air regeneration of nano-zeolite cracking catalyst may be passed out of the steam catalytic cracking reactor 200 through line 430 and may be analyzed by an in-line gas analyzer connected via line 430 to detect the presence or concentration of carbon dioxide produced through decoking of the nano-zeolite cracking catalyst. Once the carbon dioxide concentration in the gases passing out of the steam catalytic cracking reactor 200 are reduced to less than 0.05% to 0.1% by weight, as determined by the in-line gas analyzer, the temperature of the steam catalytic cracking reactor 200 temperature may be decreased from the regeneration temperature back to the reaction temperature. The airflow through line 14 may be stopped. Nitrogen gas may be passed through the nano-zeolite cracking catalyst for 15 to 30 minutes. Nitrogen gas may be stopped by closing the line 14. After closing the line 14, the flow of the deasphalted oil stream 12 and water 120 may be resumed to begin another conversion cycle of steam catalytic cracking reactor 200.

Referring again to FIG. 2, the steam catalytic cracking effluent 21 may pass out of the steam catalytic cracking reactor 200. The steam catalytic cracking effluent 21 may include one or more products and intermediates, such as but not limited to light hydrocarbon gases, olefins, aromatic compounds, pyrolysis oil, or combinations of these. Olefins in the steam catalytic cracking effluent 21 may include ethylene, propylene, butenes, or combinations of these.

The steam catalytic cracking system 20 may be disposed upstream of the steam catalytic cracking effluent separation system 250. When the steam catalytic cracking system 20 includes a plurality of steam catalytic cracking reactors 200, the steam catalytic cracking effluents 21 from each of the steam catalytic cracking reactors 200 may be passed to a single shared steam catalytic cracking effluent separation system 250. In embodiments, each steam catalytic cracking reactor 200 may have a dedicated steam catalytic cracking effluent separation system 250. The steam catalytic cracking effluent 21 may be passed from the steam catalytic cracking reactor 200 directly to the steam catalytic cracking effluent separation system 250. The steam catalytic cracking effluent separation system 250 may separate the steam catalytic cracking effluent 21 into one or more than one cracking product effluents, which may be gaseous or liquid effluents.

In embodiments where the steam catalytic cracking effluent separation system 250 comprises both a gas and liquid separation unit 30 and liquid and liquid separation unit 40, the liquid and liquid separation unit 40 may be disposed downstream of the gas and liquid separation unit 30. The gas and liquid separation unit 30 may operate to separate the steam catalytic cracking effluent 21 into a gaseous effluent 31 and liquid effluent 32. The gas and liquid separation unit 30 may operate to reduce the temperature of the steam catalytic cracking effluent 21 to condense constituents of the steam catalytic cracking effluent 21 having greater than or equal to 5 carbon atoms. The gas and liquid separation unit 30 may operate at a temperature of from 10° C. to 15° C. to ensure that normal pentane and constituents with boiling point temperatures greater than normal pentane are condensed into the liquid effluent 32. The liquid effluent 32 may include light distillation fractions such as naphtha, kerosene, gas oil, vacuum gas oil; unconverted feedstock; water; or combinations of these. The liquid effluent 32 may include at least 95%, at least 98%, at least 99%, or even at least 99.5% of the hydrocarbon constituents of the steam catalytic cracking effluent 21 having greater than or equal to 5 carbon atoms. The liquid effluent 32 may include at least 95%, at least 98%, at least 99%, or even at least 99.5% of the water from of the steam catalytic cracking effluent 21.

The gaseous effluent 31 may include olefins, such as ethylene, propylene, butenes, or combinations of these; light hydrocarbon gases, such as methane, ethane, propane, n-butane, i-butane, or combinations of these; other gases, such as but not limited to hydrogen; or combinations of these. The gaseous effluent 31 may include the $C_2$-$C_4$ olefin products, such as but not limited to, ethylene, propylene, butenes (1-butene, cis-2-butene, trans-2-butene, isobutene, or combinations of these), or combinations of these, produced in the steam catalytic cracking reactor 200. The gaseous effluent 31 may include at least 90%, at least 95%, at least 98%, at least 99%, or at least 99.5% of the $C_2$-$C_4$ olefins from the steam catalytic cracking effluent 21. The gaseous effluent 31 may be passed to a downstream gas separation system for further separation of the gaseous effluent 31 into various product streams, such as but not limited to one or more olefin product streams.

The liquid effluent 32, which includes the aqueous effluent 42 and liquid hydrocarbon effluent 41 having greater than 5 carbon atoms, may be passed to the liquid and liquid separation unit 40. The liquid and liquid separation unit 40 may operate to separate the liquid effluent 32 into the liquid hydrocarbon effluent 41 and aqueous effluent 42. The liquid and liquid separation unit 40 may be a centrifuge that is operated at a rotational speed of from 2500 rpm to 5000 rpm, from 2500 rpm to 4500 rpm, from 2500 rpm to 4000 rpm, from 3000 rpm to 5000 rpm, from 3000 rpm to 4500 rpm, or from 3000 rpm to 4000 rpm to separate the hydrocarbon phase from the aqueous phase.

The liquid hydrocarbon effluent 41 may include hydrocarbons from the steam catalytic cracking effluent 21 having greater than or equal to 5 carbon atoms. These hydrocarbons may include naphtha, kerosene, diesel, vacuum gas oil (VGO), or combinations of these. The liquid hydrocarbon effluent 41 may include at least 90%, at least 95%, at least 98%, at least 99%, or even at least 99.5% of the hydrocarbon constituents from the liquid effluent 32. The liquid hydrocarbon effluent 41 may be passed to a downstream treatment process for further conversion or separation. At least a portion of the liquid hydrocarbon effluent 41 may be passed back to the steam catalytic cracking reactor 200 for further conversion to olefins. The aqueous effluent 42 may include water and water soluble constituents from the liquid effluent 32. The aqueous effluent 42 may include some dissolved hydrocarbons soluble in the aqueous phase of the liquid effluent 32. The aqueous effluent 42 may include at least 95%, at least 98%, at least 99%, or even at least 99.5% of the water from the liquid effluent 32. The aqueous effluent 42 may be passed to one or more downstream processes for further treatment. In embodiments, at least a portion of the aqueous effluent 42 may be passed back to the steam catalytic cracking reactor 200 as at least a portion of the water 120 introduced to the steam catalytic cracking reactor 200.

Referring again to FIG. 1, the system 100 for converting a hydrocarbon feed 101 to olefins may include the SDA 10, the steam catalytic cracking system 20 downstream of the SDA 10, the gas and liquid separation unit 30 downstream of the steam catalytic cracking system 20, and the liquid and liquid separation unit 40 downstream of the gas and liquid separation unit 30. The hydrocarbon feed 101 may be introduced into the SDA 10. As previously discussed, the SDA 10 may operate to separate and remove asphaltene from the hydrocarbon feed 101 producing the deasphalted oil stream 12. The SDA 10 may be in fluid communication with the steam catalytic cracking system 20 to pass the deasphalted oil stream 12 to the steam catalytic cracking system 20. The deasphalted oil stream 12 may be introduced into the steam catalytic cracking system 20. The steam catalytic cracking system 20 may steam catalytic crack the deasphalted oil stream 12 in the presence of steam 13 and the nano-zeolite cracking catalyst to produce the steam catalytic cracking effluent 21. The gas and liquid separation unit 30 may be in fluid communication with the steam catalytic cracking system 20 to pass the steam catalytic cracking effluent 21 to the gas and liquid separation unit 30. The steam catalytic cracking effluent 21 may be introduced into the gas and liquid separation unit 30 to separate the gas effluent 31 and liquid effluent 32. The gas effluent 31 may include olefins. The liquid and liquid separation unit 40 may be in fluid communication with the gas and liquid separation unit 30 to pass the liquid effluent 32 to the liquid and liquid separation unit 40. The liquid effluent 32 may be introduced to the liquid and liquid separation unit 40 to separate the liquid effluent 32 into the liquid hydrocarbon effluent 41 and aqueous effluent 42.

The processes according to embodiments shown in FIG. 1 may achieve an olefin yield of from 40 to 80 wt. %, 40 to 70 wt. %, or 40 to 60 wt. %. The process may produce the volume ratio of propylene to ethylene from 0.5 to 3.0, 0.5 to 2.5, 1.0 to 3.0 or 1.0 to 2.5. The process may produce surplus hydrogen in the range of 1 to 15 wt. %, 5 to 10 wt. %, 10 to 15 wt. % of the steam catalytic cracking effluent 21.

Figure 3:
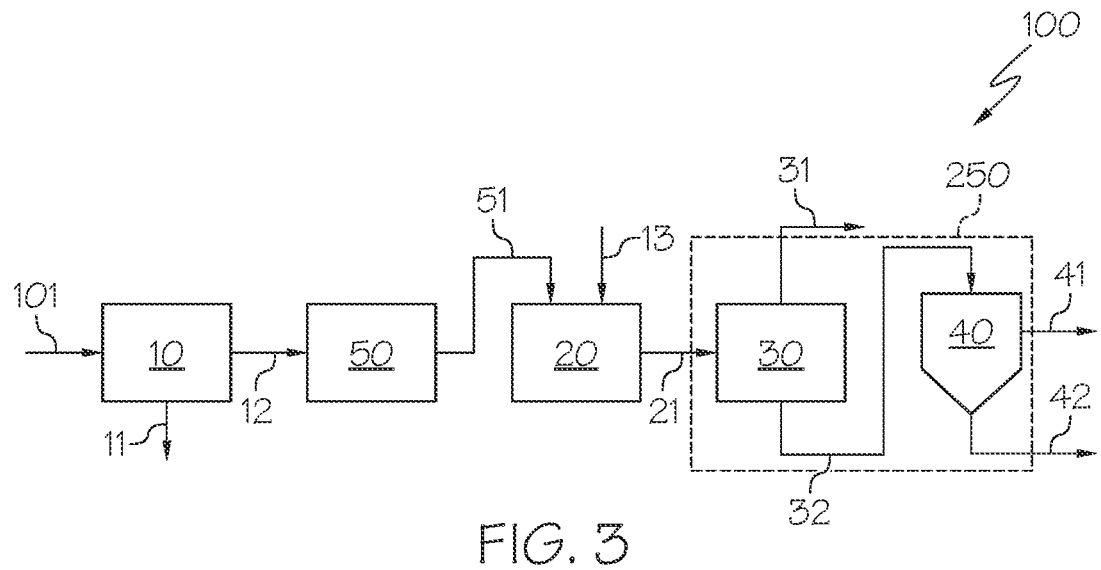
FIG. 3 schematically depicts a generalized flow diagram of another embodiment of a system for separating and upgrading crude oil, according to one or more embodiments shown and described in this disclosure.

Referring now to FIG. 3, the system 100 may further include an ultra deasphalting unit 50. The ultra deasphalting unit 50 may be disposed downstream of the SDA 10. The ultra deasphalting unit 50 may be disposed upstream of the steam catalytic cracking system 20. The ultra deasphalting unit 50 may operate to remove at least a portion of asphaltenes in the deasphalted oil stream 12 to produce an ultra deasphalted oil stream 51. The ultra deasphalting unit 50 may be in fluid communication with the steam catalytic cracking system 20 to pass the ultra deasphalted oil stream 51 to the steam catalytic cracking system 20. The steam catalytic cracking system 20 operates in the same manner as described above, except that the ultra deasphalted oil stream 51 is introduced to the catalytic cracking system 20 in place of the deasphalted oil stream depicted in FIG. 2.

The ultra-deasphalting unit 50 contains adsorption solid material. The ultra-deasphalting unit 50 may contain adsorption solid material including alumina coated with nickel oxide or alumina oxide coated with nickel oxide. The alumina or the alumina oxide may be beads ranging in size from 1 to 10 mm, 2 to 10 mm, 3 to 10 mm, 1 to 9 mm, 2 to 9 mm, 3 to 9 mm, 1 to 8 mm, 2 to 8 mm, or 3 to 8 mm. The nickel oxide may be present in an amount from at least 5 to 30 wt. %, 5 to 25 wt. %, 5 to 20 wt. %, 10 to 30 wt. %, 10 to 25 wt. %, 10 to 20 wt. % of the adsorption solid material.

The ultra-deasphalting unit 50 may adsorb asphaltene from the deasphalted oil stream 12 in the range of 100 ppm to 3000 ppm, 200 ppm to 3000 ppm, 300 ppm to 3000 ppm, 400 ppm to 3000 ppm, 500 ppm to 3000 ppm, 100 ppm to 2500 ppm, 200 ppm to 2500 ppm, 300 ppm to 2500 ppm, 400 ppm to 2500 ppm, or 500 ppm to 2500 ppm.

The weight ratio of the adsorption solid material to the deasphalted oil stream 12 in the ultra-deasphalting unit 50 may be from 0.001 to 0.02, from 0.002 to 0.02, from 0.005 to 0.02, from 0.002 to 0.01, or from 0.05 to 0.01.

Still referring to FIG. 3, in operation of the system 100 for converting the hydrocarbon feed 101 to olefins, the hydrocarbon feed 101 may be introduced into the SDA 10. The SDA 10 may operate to separate and remove asphaltene from the hydrocarbon feed 101 producing the deasphalted oil stream 12. The SDA 10 may be in fluid communication with the ultra deasphalting unit 50 to pass the deasphalted oil stream 12 to the ultra deasphalting unit 50. The ultra deasphalting unit 50 may operate to remove at least a portion of asphaltenes in the deasphalted oil stream 12 to produce the ultra deasphalted oil stream 51. The ultra deasphalting unit 50 may be in fluid communication with the steam catalytic cracking system 20 to pass the ultra deasphalted oil stream 51 to the steam catalytic cracking system 20. The steam catalytic cracking system 20 may steam catalytic crack the ultra deasphalted oil stream 51 in the presence of steam 13 and the nano-zeolite cracking catalyst to produce the steam catalytic cracking effluent 21. The gas and liquid separation unit 30 may be in fluid communication with the steam catalytic cracking system 20 to pass the steam catalytic cracking effluent 21 to the gas and liquid separation unit 30. The steam catalytic cracking effluent 21 may be introduced into the gas and liquid separation unit 30 to separate the gas effluent 31 and liquid effluent 32. The gas effluent 31 may include olefins. The liquid and liquid separation unit 40 may be in fluid communication with the gas and liquid separation unit 30 to pass the liquid effluent 32 to the liquid and liquid separation unit 40. The liquid effluent 32 may be introduced to the liquid and liquid separation unit 40 to separate the liquid effluent 32 into the liquid hydrocarbon fractions 41 and aqueous effluent 42.

The processes according to embodiments shown in FIG. 3 may achieve an olefin yield of from 40 to 80 wt. %, 40 to 70 wt. %, or 40 to 60 wt. %. The process may produce the volume ratio of propylene to ethylene from 0.5 to 3.0, 0.5 to 2.5, 1.0 to 3.0 or 1.0 to 2.5. The process may produce surplus hydrogen in the range of 1 to 15 wt. %, 5 to 10 wt. %, 10 to 15 wt. % of the steam catalytic cracking effluent 21.

Figure 4:
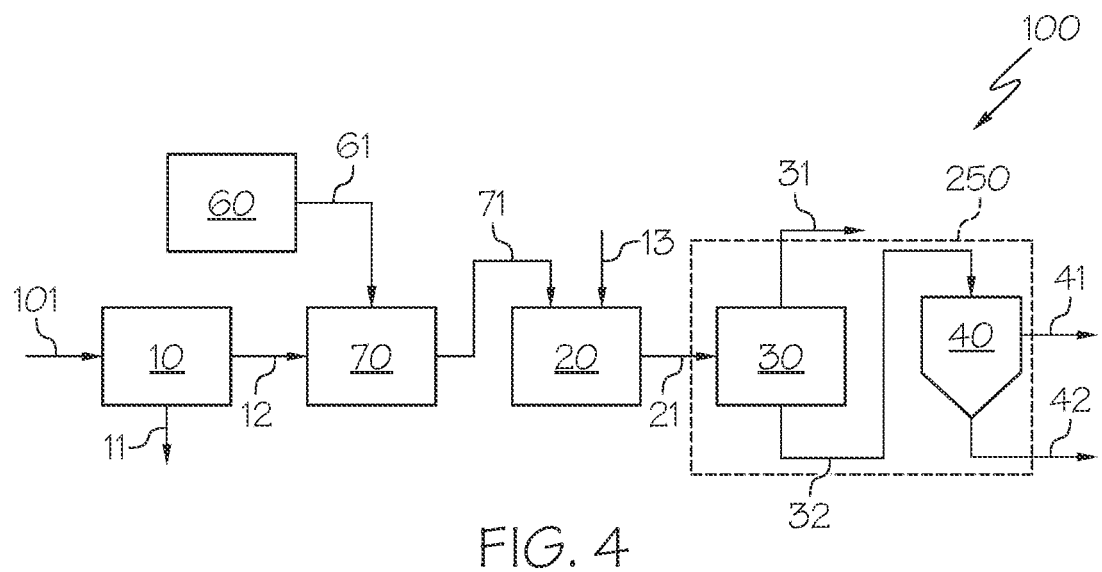
FIG. 4 schematically depicts a generalized flow diagram of still another embodiment of a system for separating and upgrading crude oil, according to one or more embodiments shown and described in this disclosure.

Referring now to FIG. 4, the system 100 may further include a gas plant 60 and a feed blending unit 70. The gas plant 60 may be disposed upstream of the feed blending unit 70. The gas plant 60 may operate to introduce a gas condensate 61 to the feed blending unit 70. The gas plant 60 may be in fluid communication with the feed blending unit 70 to pass the gas condensate 61 to the feed blending unit 70.

The feed blending unit 70 may operate to mix the gas condensate 61 and the deasphalted oil stream 12 producing the blended deasphalted oil stream 71. The mixture of the gas condensate 61 and the deasphalted oil stream 12 may enhance the yield of olefins as well as the selectivity of propylene and butenes. The mixture of the gas condensate 61 and the deasphalted oil stream 12 may increase the ratio of propylene/ethylene.

The gas condensate 61 may be a liquid hydrocarbon stream. The gas condensate 61 may comprise distillation fractions, such as naphtha, kerosene, gas oil, or combinations thereof. In embodiments, the gas condensate 61 may be a gas condensate produced from the Khuff geological formation. When the gas condensate 61 comprises a Khuff gas condensate, the gas condensate 61 may include about 3.6 wt. % C4 fraction, 15.5 wt. % light naphtha, 28.3 wt. % middle naphtha, 15 wt. % heavy naphtha fraction, 15.7 wt. % kerosene, and 21.9 wt. % gas oil. The gas condensate 61 may have an API gravity of from 50 degrees to 60 degrees, or from 50 degrees to 58 degrees. The gas condensate 61 may have sulfur content of from 0.01 to 0.2 wt. %, from 0.02 to 0.2 wt. %, or from 0.01 to 0.1 wt. %. When the gas condensate 61 comprises a Khuff gas condensate, the gas condensate 61 may have an API gravity of 53.9 degrees and sulfur content of 0.04 wt. %.

Referring again to FIG. 4, the total feed to the steam catalytic cracking system 20 may include from 5 wt. % to 50 wt. % gas condensate 61 based on the total flow rate of hydrocarbons (gas condensate 61 and the deasphalted oil stream 12) passed to the steam catalytic cracking system 20. In embodiments, the total hydrocarbon feed to the steam catalytic cracking system 20 may include from 10 wt. % to 50 wt. %, from 15 wt. % to 50 wt. %, from 20 wt. % to 50 wt. %, from 5 wt. % to 45 wt. %, from 5 wt. % to 40 wt. %, from 10 wt. % to 45 wt. %, from 10 wt. % to 40 wt. %, from 15 wt. % to 45 wt. %, or from 15 wt. % to 40 wt. % gas condensate 61 based on the total flow rate of gas condensate 61 and deasphalted oil stream 12 passed to the steam catalytic cracking system 20.

The feed blending unit 70 may be disposed downstream of the SDA 10. The feed blending unit 70 may be upstream of the steam catalytic cracking system 20. The feed blending unit 70 may operate to blend the gas condensate 61 and the deasphalted oil stream 12 to produce the blended deasphalted oil stream 71.

Still referring to FIG. 4, in operation of the system 100 for converting the hydrocarbon feed 101 to olefins, the hydrocarbon feed 101 may be introduced into the SDA 10. The SDA 10 may operate to separate and remove asphaltene from the hydrocarbon feed 101 producing the deasphalted oil stream 12. The SDA 10 may be in fluid communication with the feed blending unit 70 to pass the deasphalted oil stream 12 to the feed blending unit 70. The gas plant 60 may be in fluid communication with the feed blending unit 70 to pass the gas condensate 61 to the feed blending unit 70. The deasphalted oil stream 12 and the gas condensate 61 may be blended in the feed blending unit 70 to produce the blended deasphalted oil stream 71. The feed blending unit 70 may be in fluid communication with the steam catalytic cracking system 20 to pass the blended deasphalted oil stream 71 to the steam catalytic cracking system 20. The steam catalytic cracking system 20 may steam catalytic crack the blended deasphalted oil stream 71 in the presence of steam 13 and the nano-zeolite cracking catalyst to produce the steam catalytic cracking effluent 21. The gas and liquid separation unit 30 may be in fluid communication with the steam catalytic cracking system 20 to pass the steam catalytic cracking effluent 21 to the gas and liquid separation unit 30. The steam catalytic cracking effluent 21 may be introduced into the gas and liquid separation unit 30 to separate the gas effluent 31 and liquid effluent 32. The gas effluent 31 may include olefins. The liquid and liquid separation unit 40 may be in fluid communication with the gas and liquid separation unit 30 to pass the liquid effluent 32 to the liquid and liquid separation unit 40. The liquid effluent 32 may be introduced to the liquid and liquid separation unit 40 to separate the liquid effluent 32 into the liquid hydrocarbon fractions 41 and aqueous effluent 42.

The processes according to embodiments shown in FIG. 4 may achieve an olefin yield of from 40 to 80 wt. %, 40 to 70 wt. %, or 40 to 60 wt. %. The process may produce the volume ratio of propylene to ethylene from 0.5 to 3.0, 0.5 to 2.5, 1.0 to 3.0 or 1.0 to 2.5. The process may produce surplus hydrogen in the range of 1 to 15 wt. %, 5 to 10 wt. %, 10 to 15 wt. % of the steam catalytic cracking effluent 21.

Figure 5:
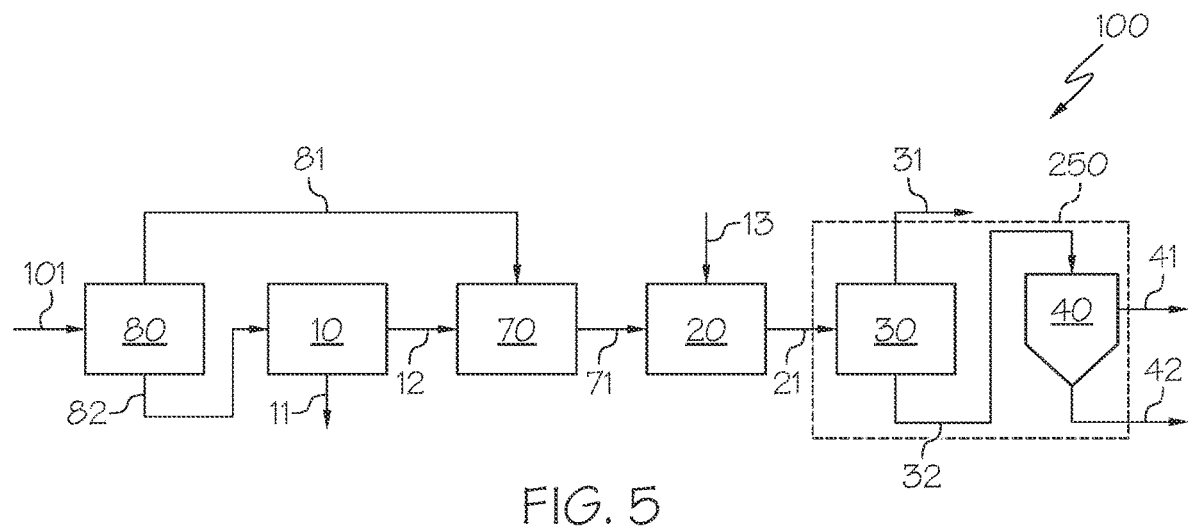
FIG. 5 schematically depicts a generalized flow diagram of another embodiment of a system for separation and upgrading crude oil, according to one or more embodiments shown and described in this disclosure.

Referring now to FIG. 5, the system 100 may further include a feed topping unit 80. The feed topping unit 80 may be disposed upstream of the SDA 10 and the feed blending unit 70. The other units in the system 100 depicted in FIG. 5 (i.e., the SDA 10, the feed blending unit 70, the steam catalytic cracking system 20, the gas and liquid separation unit 30, and the liquid and liquid separation unit 40) operate as described above.

According to embodiments, the feed topping unit 80 may operate to conduct distillation at 90 to 100° C., or 90 to 95° C. to separate hydrocarbon feed 101 into a low boiling point fraction 81, such as a light naphtha fraction, and a high boiling point fraction 82, such as a reduced hydrocarbon feed. The amount of low boiling point fraction 81 may be 5 to 15 wt. %, or 5 to 10 wt. %. The amount of high boiling point fraction 82 may be 85 to 95 wt. %, or 85 to 90 wt. %. In one or more embodiments, the feed topping unit 80 may operate to conduct distillation at 150 to 170° C., or 150 to 160° C. to separate hydrocarbon feed 101 into a low boiling point fraction 81, such as the light and middle naphtha fraction, and high boiling point fraction 82, such as reduced hydrocarbon feed. The amount of low boiling point fraction 81 may be 25 to 35 wt. %, or 25 to 30 wt. %. The amount of high boiling point fraction 82 may be 65 to 75 wt. %, or 65 to 70 wt. %. In embodiments, the feed topping unit 80 may operate to conduct distillation at 195 to 205° C., or 195 to 200° C. to separate hydrocarbon feed 101 into a low boiling point fraction 81, such as the light, middle, and heavy naphtha fraction, and high boiling point fraction 82, such as reduced hydrocarbon feed. The amount of low boiling point fraction 81 may be 35 to 45 wt. %, or 35 to 40 wt. %. The amount of high boiling point fraction 82 may be 55 to 65 wt. %, or 55 to 60 wt. %.

The feed topping unit 80 may be in fluid communication with the feed blending unit 70 to pass the low boiling point fraction 81 directly to the feed blending unit 70, thereby the low boiling point fraction 81 is not introduced into the SDA 10. The feed topping unit 80 may be in fluid communication with the SDA 10 to pass the high boiling point fraction 82 to the SDA 10.

The cut temperature or "cut point" (that is, the approximate atmospheric boiling point temperature separating the low boiling point fraction 81 and the high boiling point fraction 82) of the feed topping unit 80 may be from 93 degrees Celsius (° C.) to 205° C. As such, all components of the low boiling point fraction 81 may have a boiling point (at atmospheric pressure) of less than or equal to 205° C., less than or equal to 200° C., less than or equal to 150° C., less than or equal to 100° C., or less than or equal to 95° C., or even less than or equal to 93° C., and all components of the high boiling point fraction 82 may have a boiling point (at atmospheric pressure) of at least 93° C., at least 95° C., at least 100° C., at least 150° C., or at least 200° C., or even at least 205° C.

Still referring to FIG. 5, in operation of the system 100 for converting the hydrocarbon feed 101 to olefins, the hydrocarbon feed 101 may be introduced into the feed topping unit 80. The feed topping unit 80 may separate the hydrocarbon feed 101 into the low boiling point fraction 81 and high boiling point fraction 82. The high boiling point fraction 82 may be introduced into the SDA 10. The SDA 10 may operate to separate and remove asphaltene from the high boiling point fraction 82 producing the deasphalted oil stream 12. The SDA 10 may be in fluid communication with the feed blending unit 70 to pass the deasphalted oil stream 12 to the feed blending unit 70. The feed blending unit 70 may be operated to mix the deasphalted oil stream 12 and the low boiling point fraction 81 producing the blended deasphalted oil stream 71. The feed blending unit 70 may be in fluid communication with the steam catalytic cracking system 20 to pass the blended deasphalted oil stream 71 to the steam catalytic cracking system 20. The steam catalytic cracking system 20 may steam catalytic crack the blended deasphalted oil stream 71 in the presence of steam 13 and the nano-zeolite cracking catalyst to produce the steam catalytic cracking effluent 21. The steam catalytic cracking effluent 21 may be introduced into the gas and liquid separation unit 30 to separate the gas effluent 31 and liquid effluent 32. The gas effluent 31 may include olefins. The liquid and liquid separation unit 40 may be in fluid communication with the gas and liquid separation unit 30 to pass the liquid effluent 32 to the liquid and liquid separation unit 40. The liquid effluent 32 may be introduced to the liquid and liquid separation unit 40 to separate the liquid effluent 32 into the liquid hydrocarbon fractions 41 and aqueous effluent 42.

The processes according to embodiments shown in FIG. 5 may achieve an olefin yield of from 40 to 80 wt. %, 40 to 70 wt. %, or 40 to 60 wt. %. The process may produce the volume ratio of propylene to ethylene from 0.5 to 3.0, 0.5 to 2.5, 1.0 to 3.0 or 1.0 to 2.5. The process may produce surplus hydrogen in the range of 1 to 15 wt. %, 5 to 10 wt. %, 10 to 15 wt. % of the steam catalytic cracking effluent 21.

Figure 6:
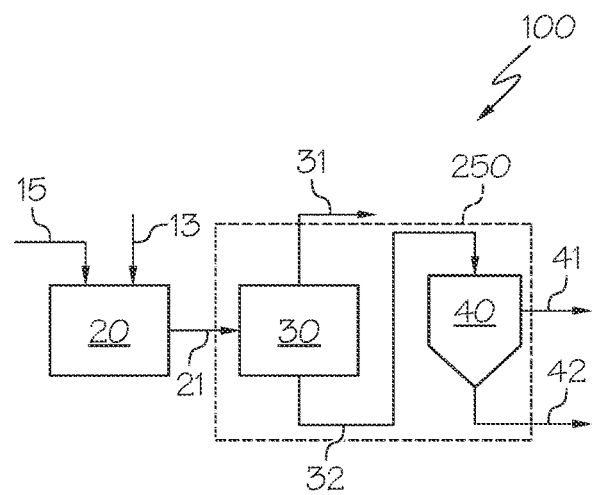
FIG. 6 schematically depicts a generalized flow diagram of another embodiment of a system for separation and upgrading crude oil, according to one or more embodiments shown and described in this disclosure.

Referring to FIG. 6, the hydrocarbon feed may be asphaltene-free whole crude oil 15. The asphaltene-free whole crude oil 15 may be introduced into the steam catalytic cracking system 20, which operates as described herein.

In embodiments, the asphaltene-free whole crude oil 15 may have an American Petroleum Institute (API) gravity of more than 40. The asphaltene-free whole crude oil 15 may have an API gravity between 26 and 52, 28 and 52, 26 and 50, or 28 and 50.

Still referring to FIG. 6, in operation of the system 100 for converting the hydrocarbon feed 101 to olefins, the asphaltene-free whole crude oil 15 may be introduced into the steam catalytic cracking system 20. The steam catalytic cracking system 20 may steam catalytic crack the asphaltene-free whole crude oil 15 in the presence of steam 13 and the nano-zeolite cracking catalyst to produce the steam catalytic cracking effluent 21. The gas and liquid separation unit 30 may be in fluid communication with the steam catalytic cracking system 20 to pass the steam catalytic cracking effluent 21 to the gas and liquid separation unit 30. The steam catalytic cracking effluent 21 may be introduced into the gas and liquid separation unit 30 to separate the gas effluent 31 and liquid effluent 32. The gas effluent 31 may include olefins. The liquid and liquid separation unit 40 may be in fluid communication with the gas and liquid separation unit 30 to pass the liquid effluent 32 to the liquid and liquid separation unit 40. The liquid effluent 32 may be introduced to the liquid and liquid separation unit 40 to separate the liquid effluent 32 into the liquid hydrocarbon fractions 41 and aqueous effluent 42.

The processes according to embodiments shown in FIG. 6 may achieve an olefin yield of from 40 to 80 wt. %, 40 to 70 wt. %, or 40 to 60 wt. %. The process may produce the volume ratio of propylene to ethylene from 0.5 to 3.0, 0.5 to 2.5, 1.0 to 3.0 or 1.0 to 2.5. The process may produce surplus hydrogen in the range of 1 to 15 wt. %, 5 to 10 wt. %, 10 to 15 wt. % of the steam catalytic cracking effluent 21.

EXAMPLES

The various embodiments of methods and systems for the processing of a hydrocarbon feed to produce olefins will be further clarified by the following examples. The examples are illustrative in nature, and should not be understood to limit the subject matter of the present disclosure.

Example 1: Converting Whole Crude Oil to Olefins

In Example 1, the steam catalytic cracking system was utilized to convert a crude oil with an API gravity of 32 to olefins. Crude oil was subjected to crude oil topping at 150° C. The crude oil was deasphalted at the SDA to produce the deasphalted oil stream. The deasphalted oil stream was sent to the steam catalytic cracking reactor. The deasphalted oil stream was steam catalytically cracked in the fixed bed reactor at 600° C. with the steam and the nano-zeolite cracking catalyst. The nano ZSM-5 with 40% alumina binder was used as the nano-zeolite cracking catalyst. The pre-heated feed at 100° C. was introduced to the reactor at a space velocity of 1 hourly ($h^{-1}$) and steam was injected at space velocity of 3 hourly ($h^{-1}$). As shown in Table 2, the high yield of olefins (50%) was achieved with propylene/ethylene ratio of 1 and propylene/butenes ratio of 3.3. Furthermore, the process produced a surplus of hydrogen (approximately 7%) and NGL+ethane in the range of approximately 7%. The whole crude oil conversion via nano zeolite steam catalytic process was performed for 230 minutes time on stream as a one conversion cycle and showed high performance and stability sustaining high olefins yield around 50%.

Example 2: Converting Whole Crude Oil to Olefins

In Example 2, the steam catalytic cracking process was utilized to convert a crude oil with an API gravity of 32 to olefins. Crude oil was subjected to crude oil topping at 150° C. The crude oil was deasphalted at the SDA to produce the deasphalted oil stream. The deasphalted oil stream was sent to the feed blending unit and mixed with the 20 wt. % of gas condensate to produce the blended deasphalted oil stream. The blended deasphalted oil stream was sent to the steam catalytic cracking unit. The blended deasphalted oil stream was steam catalytically cracked in the fixed bed reactor at 600° C. with the steam and the nano-zeolite cracking catalyst. The nano ZSM-5 with 40% alumina binder was used as the nano-zeolite cracking catalyst. The pre-heated feed at 100° C. was introduced to the reactor at a space velocity of 1 hourly ($h^{-1}$) and steam was injected at space velocity of 3 hourly ($h^{-1}$). As shown in Table 2, high yield of olefins (55%) was attained with propylene/ethylene ratio of 1.8 and propylene/butenes ratio of 2.5. Also, a hydrogen surplus (approximately 8%) was produced and about 7% NGL+ethane. The deasphalted whole crude oil blended with 20% condensate conversion via nano zeolite steam catalytic process was performed for 230 minutes time on stream as a one conversion cycle and showed high performance and stability sustaining high olefins yield around 55%.

TABLE 2

Composition of steam catalytic cracking effluent from Example 1, and Example 2

| Constituent | Example 1 Yield (wt. %) | Example 2 Yield (wt. %) |
|---|---|---|
| Naphtha, % | 3.5 | 2.5 |
| Kerosene, % | 7.0 | 5.3 |
| Diesel, % | 5.8 | 4.5 |
| VGO, % | 6.3 | 3.8 |
| Olefins, % | 50 | 55.3 |
| Ethylene, % | 22.1 | 15.9 |
| Propylene, % | 22.5 | 28 |
| Butenes, % | 6.8 | 11.3 |
| P/E | 1 | 1.8 |
| $H_2$, % | 7.1 | 8.8 |
| Methane, % | 3 | 2.8 |
| NGL + Ethane gas, % | 7.4 | 7 |
| Coke | 3.3 | 1.4 |

A first aspect of the present disclosure is directed to a process for producing olefins from a hydrocarbon feed that may include introducing the hydrocarbon feed into a Solvent Deasphalting Unit (SDA) to remove asphaltene from the hydrocarbon feed producing a deasphalted oil stream, wherein the SDA comprises a solvent that reacts with the hydrocarbon feed, and the deasphalted oil stream comprises from 0.01 weight percent (wt. %) to 18 wt. % asphaltenes; introducing the deasphalted oil stream into a steam catalytic cracking system; steam catalytically cracking the deasphalted oil stream in the steam catalytic cracking system in the presence of steam and a nano zeolite cracking catalyst to produce a steam catalytic cracking effluent; and separating the olefins from the steam catalytic cracking effluent.

A second aspect of the present disclosure may include the first aspect, wherein a solvent-to-hydrocarbon feed volume ratio in the SDA is from 2:1 to 50:1.

A third aspect of the present disclosure may include either one of the first or second aspects, wherein the deasphalted oil stream has an American Petroleum Institute (API) gravity between 26 and 52.

A fourth aspect of the present disclosure may include any one of the first through third aspects, wherein the deasphalted oil stream is steam catalytically cracked at a reaction temperature of from 550 degrees Celsius (° C.) to 750° C.

A fifth aspect of the present disclosure may include any one of the first through fourth aspects, wherein the nano zeolite cracking catalyst comprises nano ZSM-5 zeolite, nano BEA zeolite, or a combination thereof.

A sixth aspect of the present disclosure may include any one of the first through fifth aspects, wherein the nano zeolite cracking catalyst has a silica to alumina molar ratio from 10:1 to 200:1.

A seventh aspect of the present disclosure may include any one of the first through sixth aspects, wherein a crystal size of the nano zeolite cracking catalyst is from 50 nanometer (nm) to 600 nm.

An eighth aspect of the present disclosure may include any one of the first through seventh aspects, wherein an olefin yield from the process is from 40 mol. % to 80 mol. %.

A ninth aspect of the present disclosure may include any one of the first through eighth aspects, wherein the olefins comprise ethylene, propylene, butene, and combinations thereof.

A tenth aspect of the present disclosure may include any one of the first through ninth aspects, wherein the olefins comprise propylene and butene, and a volume ratio of propylene to butene is from 0.5 to 3.0.

An eleventh aspect of the present disclosure may include any one of the first through tenth aspects, further comprising: introducing the deasphalted oil stream into an ultra deasphalting unit to remove at least a portion of asphaltenes in the deasphalted oil stream to produce an ultra deasphalted oil stream, wherein the ultra deasphalted oil stream has an asphaltene content in a range of 100 parts per million (ppm) to 3000 ppm upon exiting the ultra deasphalting unit.

A twelfth aspect of the present disclosure may include the eleventh aspect, wherein the ultra deasphalting unit contains adsorption solid material comprising alumina coated with nickel oxide, or alumina oxide coated with nickel oxide, wherein the nickel oxide is present in an amount from at least 5 to 30 wt. % of the adsorption solid material.

A thirteenth aspect of the present disclosure may include the twelfth aspect, wherein the alumina oxide has a size of from 1 millimeter (mm) to 10 mm.

A fourteenth aspect of the present disclosure may include the twelfth aspect, wherein a weight ratio of the adsorption solid material to the deasphalted oil stream is from 0.001 to 0.02.

A fifteenth aspect of the present disclosure may include any one of the first through fourteenth aspects, further comprising: mixing the deasphalted oil stream with a gas condensate upstream from the steam catalytically cracking of the deasphalted oil stream, wherein the content of the gas condensate is from 5 wt. % to 25 wt. % of the deasphalted oil stream.

A sixteenth aspect of the present disclosure may include any one of the first through fifteenth aspects, further comprising: separating the hydrocarbon feed into at least a low boiling point fraction and a high boiling point fraction; introducing the high boiling point fraction into the SDA to remove asphaltene from the high boiling point fraction thereby producing a deasphalted oil stream, wherein the SDA comprises a solvent that reacts with the high boiling point fraction, and the deasphalted oil stream comprises from 0.01 wt. % to 18 wt. %; and mixing the deasphalted oil stream with the low boiling point fraction upstream from steam catalytically cracking of the deasphalted oil stream.

A seventeenth aspect of the present disclosure may include the sixteenth aspect, wherein a cut point of the low boiling point fraction and the high boiling point fraction is from 93° C. to 205° C.

An eighteenth aspect of the present disclosure may include any one of the first through seventeenth aspects, wherein the separating the olefins comprises: separating gas effluent and liquid effluent from the steam catalytic cracking effluent, wherein the gas effluent comprises the olefins, methane, ethane, propane, butane, or combinations thereof; and separating liquid hydrocarbon effluent and aqueous effluent from the liquid effluent, where the liquid hydrocarbon effluent comprises naphtha, kerosene, diesel, vacuum gas oil, or combinations thereof.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for producing olefins from a hydrocarbon feed, the process comprising:
   introducing at least a portion of the hydrocarbon feed into a Solvent Deasphalting Unit (SDA) to remove asphaltene from the hydrocarbon feed producing a deasphalted oil stream, wherein the SDA comprises a solvent that reacts with the hydrocarbon feed, and the deasphalted oil stream comprises from 0.01 weight percent (wt. %) to 18 wt. % asphaltenes;
   introducing the deasphalted oil stream into an ultra deasphalting unit to remove at least a portion of asphaltenes in the deasphalted oil stream to produce an ultra deasphalted oil stream, wherein the ultra deasphalting unit contains adsorption solid material comprising alumina coated with nickel oxide, wherein the nickel oxide is present in an amount from at least 5 to 30 wt. % of the adsorption solid material, the alumina has a size of from 1 millimeter (mm) to 10 mm;
   introducing the ultra deasphalted oil stream into a steam catalytic cracking system;
   steam catalytically cracking the ultra deasphalted oil stream in the steam catalytic cracking system in the presence of steam and a nano zeolite cracking catalyst to produce a steam catalytic cracking effluent; and
   separating the olefins from the steam catalytic cracking effluent.

2. The process of claim 1, wherein a solvent-to-hydrocarbon feed volume ratio in the SDA is from 2:1 to 50:1.

3. The process of claim 1, wherein the deasphalted oil stream has an American Petroleum Institute (API) gravity between 26 and 52.

4. The process of claim 1, wherein the ultra deasphalted oil stream is steam catalytically cracked at a reaction temperature of from 550 degrees Celsius (° C.) to 750° C.

5. The process of claim 1, wherein the nano zeolite cracking catalyst comprises nano ZSM-5 zeolite, nano BEA zeolite, or a combination thereof.

6. The process of claim 1, wherein the nano zeolite cracking catalyst has a silica to alumina molar ratio from 10:1 to 200:1.

7. The process of claim 1, wherein a crystal size of the nano zeolite cracking catalyst is from 50 nanometer (nm) to 600 nm.

8. The process of claim 1, where an olefin yield from the process is from 40 mol. % to 80 mol. %.

9. The process of claim 1, wherein the olefins comprise ethylene, propylene, butene, or combinations thereof.

10. The process of claim 1, wherein the olefins comprise propylene and butene, and a volume ratio of propylene to butene is from 0.5 to 3.0.

11. The process of claim 1, wherein a weight ratio of the adsorption solid material to the deasphalted oil stream is from 0.001 to 0.02.

12. The process of claim 1, further comprising:
   mixing the deasphalted oil stream with a gas condensate upstream from the steam catalytically cracking of the deasphalted oil stream, wherein the content of the gas condensate is from 5 wt. % to 25 wt. % of the deasphalted oil stream.

13. The process of claim 1, further comprising:
   separating the hydrocarbon feed into at least a low boiling point fraction and a high boiling point fraction;
   introducing the high boiling point fraction into the SDA to remove asphaltene from the high boiling point fraction thereby producing a deasphalted oil stream, wherein the SDA comprises a solvent that reacts with the high boiling point fraction, and the deasphalted oil stream comprises from 0.01 wt. % to 18 wt. %; and
   mixing the deasphalted oil stream with the low boiling point fraction upstream from steam catalytically cracking of the deasphalted oil stream.

14. The process of claim 13, wherein a cut point of the low boiling point fraction and the high boiling point fraction is from 93° C. to 205° C.

15. The process of claim 1, wherein the separating the olefins comprises:
   separating gas effluent and liquid effluent from the steam catalytic cracking effluent, wherein the gas effluent comprises the olefins, methane, ethane, propane, butane, or combinations thereof; and
   separating liquid hydrocarbon effluent and aqueous effluent from the liquid effluent, where the liquid hydrocarbon effluent comprises naphtha, kerosene, diesel, vacuum gas oil, or combinations thereof.

16. A process for producing olefins from a hydrocarbon feed, the process comprising:
   introducing at least a portion of the hydrocarbon feed into a Solvent Deasphalting Unit (SDA) to remove asphaltene from the hydrocarbon feed producing a deasphalted oil stream, wherein the SDA comprises a solvent that reacts with the hydrocarbon feed, and the deasphalted oil stream comprises from 0.01 weight percent (wt. %) to 18 wt. % asphaltenes;
   introducing the deasphalted oil stream into an ultra deasphalting unit to remove at least a portion of asphaltenes in the deasphalted oil stream to produce an ultra deasphalted oil stream, wherein the ultra deasphalting unit contains adsorption solid material comprising alumina coated with nickel oxide, wherein the nickel oxide is present in an amount from at least 5 to 30 wt. % of the adsorption solid material, the alumina has a size of from 1 millimeter (mm) to 10 mm;
   introducing the ultra deasphalted oil stream into a steam catalytic cracking system;
   steam catalytically cracking the ultra deasphalted oil stream in the steam catalytic cracking system in the presence of steam and a nano zeolite cracking catalyst to produce a steam catalytic cracking effluent, wherein the flowrate of steam is from 2 to 10 times greater than the flowrate of deasphalted oil stream; and
   separating the olefins from the steam catalytic cracking effluent.

* * * * *